US00PP25424P2

(12) United States Plant Patent
Hartman

(10) Patent No.: US PP25,424 P2
(45) Date of Patent: Apr. 7, 2015

(54) ***CALADIUM* PLANT NAMED 'PUPPY LOVE'**

(50) Latin Name: *Caladium×hortulanum*
Varietal Denomination: Puppy Love

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 134 days.

(21) Appl. No.: 13/986,555

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Puppy Love', characterized by its compact, upright and uniformly mounding plant habit; vigorous growth habit; lance-type leaves that are rose red in color with rose red-colored venation and green to whitish green-colored margins; and good landscape performance.

4 Drawing Sheets

Botanical designation: *Caladium×hortulanum.*
Cultivar denomination: 'PUPPY LOVE'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'Puppy Love'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in May, 2007 in Avon Park, Fla. of *Caladium×hortulanum* 'John Peed', not patented, as the female, or seed, parent with a proprietary selection of *Caladium×hortulanum* identified as code number WS-02-18, not patented, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Puppy Love'. These characteristics in combination distinguish 'Puppy Love' as a new and distinct *Caladium* plant:

1. Compact, upright and uniformly mounding plant habit.
2. Vigorous growth habit.
3. Lance-type leaves that are rose red in color with rose red-colored venation and green to whitish green-colored margins.
4. Good landscape performance.

Plants of the new *Caladium* differ primarily from plants of the female parent, 'John Peed', in leaf shape and color as plants of 'John Peed' have fancy-type leaves that are dark green in color with red-colored venation. In addition, plants of the new *Caladium* are more compact than plants of 'John Peed'.

Plants of the new *Caladium* differ primarily from plants of the male parent selection in leaf color as leaves of plants of the male parent selection are white and greyed white in color with a variable pink-colored blush and green-colored margins. In addition, plants of the new *Caladium* and the male parent selection differ in leaf petiole color as plants of the male parent selection have green-colored leaf petioles with dark green-colored stippling and streaks.

Plants of the new *Caladium* can be compared to plants of *Caladium×hortulanum* 'Florida Sweetheart', disclosed in U.S. Plant Pat. No. 8,526. In side-by-side comparisons, plants of the new *Caladium* differed primarily from plants of 'Florida Sweetheart' in the following characteristics:

1. Plants of the new *Caladium* grew faster and produced finished plants about one week earlier than plants of 'Florida Sweetheart'.
2. Plants of the new *Caladium* and 'Florida Sweetheart' differed in leaf luster and coloration as leaves of plants of 'Florida Sweetheart' were duller and had lighter rose red-colored centers and dark green-colored margins.
3. Plants of the new *Caladium* had flatter leaves than plants of 'Florida Sweetheart'.

Plants of the new *Caladium* can be compared to plants of *Caladium×hortulanum* 'Pink Symphony', not patented. In side-by-side comparisons, plants of the new *Caladium* differed primarily from plants of 'Pink Symphony' in the following characteristics:

1. Plants of the new *Caladium* were more compact than plants of 'Pink Symphony'.
2. Plants of the new *Caladium* grew faster and produced finished plants about one to two weeks earlier than plants of 'Pink Symphony'.
3. Plants of the new *Caladium* and 'Pink Symphony' differed in leaf luster and coloration as leaves of plants of 'Pink Symphony' were duller with mostly pink or pale pink-colored centers surrounded by a green-colored border with white to greenish white-colored venation.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Puppy Love' in a 15-cm container and grown in a shadehouse.

The photograph at the top of the second sheet is a comparison view of typical plants of 'Puppy Love' grown in 15-cm containers; the plant on the left has not had its tuber de-eyed and the plant on the right has had its tuber de-eyed prior to planting.

The photograph at the bottom of the second sheet is a close-up view of a typical inflorescence of 'Puppy Love'.

The photograph at the top of the third is a close-up view of typical freshly-harvested tubers and roots of 'Puppy Love'.

The photograph at the bottom of the third sheet is a view of typical plants of 'Flare' grown in an open field.

The photograph at the top of the fourth sheet is a comparison view of typical potted plants of 'Florida Sweetheart' (left), 'Puppy Love' (center) and 'Pink Symphony' (right).

The photograph at the bottom of the fourth sheet is a comparison view of typical potted plants of the male parent selection (left), 'Puppy Love' (center) and the female parent, 'John Peed' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were nine weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Puppy Love'.

Parentage:

*Female, or seed, parent.*—*Caladium×hortulanum* 'John Peed', not patented.

*Male, or pollen, parent.*—Proprietary selection of *Caladium×hortulanum* identified as code number WS-02-18, not patented.

PROPAGATION:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate to rounded in shape. Height: About 3.1 cm. Diameter: About 3.5 cm to 3.8 cm. Segment height: About 1.9 cm to 2.1 cm. Segment diameter: About 3 cm. Texture: Thick, starchy; somewhat brittle. Color: Epidermis, freshly-harvested: Close to 199B and 200B. Epidermis, dried: Close to 200A to 200B. Cortical tissue: Close to 2D. Axillary buds: Close to 27B to 27C. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Compact, upright and uniformly mounding plant habit; vigorous and dense growth habit; potted plants in finished or saleable form in about seven to eight weeks after planting tubers; leaf petioles and leaves arise from one or more growing points on tubers; petioles mostly upright and arching outwardly with development.

*Plant height, from soil level to top of foliar plane, shadehouse-grown potted plants.*—About 17 cm to 19 cm.

*Plant height, from soil level to top of inflorescences, shadehouse-grown potted plants.*—About 27 cm.

*Plant diameter or spread, shadehouse-grown potted plants.*—About 31 cm to 38 cm.

*Number of clumps per plant, shadehouse-grown potted plants.*—About four from de-eyed tubers.

*Cataphylls, shadehouse-grown potted plants.*—Length: About 3 cm to 5 cm. Width: About 1.5 cm. Shape: Wedge-shaped. Apex: Acuminate to acute. Base: Sheathing the stem. Color, outer surface: Close to N170D tinged with close to 147C and densely variably stippled and streaked with close to 200C tinged with close to 147A; with development, color becoming closer to 200D tinged with close to 187A. Color, inner surface: Close to N155C; outer surface colors and patterns visible.

Foliage description:

*Arrangement and type.*—Alternate; simple; lance-type.

*Length, shadehouse-grown potted plants.*—About 17 cm to 20 cm.

*Width, shadehouse-grown potted plants, flattened.*—About 11 cm to 14.5 cm.

*Shape.*—Ovate to lanceolate.

*Apex.*—Acute to acuminate.

*Base.*—Sagittate, peltate; cordate.

*Margin*.—Entire; wavy with broad undulations.

*Texture, upper surface*.—Smooth, glabrous; leathery; slightly glossy in luster.

*Texture, lower surface*.—Smooth, glabrous; glaucous.

*Venation pattern*.—Pinnate.

*Color, shadehouse-grown potted plants*.—Developing leaves, upper surface: Background color: Central areas, close to 184C; marginal areas, close to 184C to 184D and 157A; margin, close to 147A. Basal notch: Close to 187A. Venation: Close to 59A to 59B and 53B. Developing leaves, lower surface: Background color: Central areas, close to 185C; transitional areas, close to 185C and 159C; marginal areas, close to 160D and 191A; margins, close to 187A. Basal notch: Close to 187A. Midvein: Close to 182B tinged and streaked with close to 183D. Primary venation: Close to 148A and 182B. Fully expanded leaves, upper surface: Background color: Central areas, close to 184B to 184C; marginal areas, close to 147A to 147B and 157A tinged with close to 184B; margin, close to 147A. Basal notch: Close to 187A. Venation: Close to 53B tinged with close to 187B Fully expanded leaves, lower surface: Background color: Central areas, close to 185C; transitional areas, close to 185D, 191A and 159C to 159D; marginal areas, close to 191A and 189A; margins, close to 187A. Basal notch: Close to 187A. Midvein: Close to 182B to 182C streaked with close to 183C to 183D. Primary venation: Close to 147B to 147C and 182A to 182B.

*Petiole*.—Aspect: Initially upright and straight; with development, leaning outwardly and curving; flexible. Length, shadehouse-grown potted plants: About 12 cm to 14 cm. Diameter, distal, shadehouse-grown potted plants: About 3.5 mm to 4 mm. Diameter, proximal, shadehouse-grown potted plants: About 6 mm to 9 mm. Color, shadehouse-grown potted plants: Close to N170D tinged with close to 182D and stippled, streaked and tessellated with close to 200C tinged with close to 147A; distally, close to 186D or 184D. Wing length, shadehouse-grown potted plants: About 2.5 cm to 4 cm. Wing diameter, shadehouse-grown potted plants: About 4 mm to 8 mm. Wing color, shadehouse-grown potted plants, outer surface: Close to N170D tinged with close to 147C and variably stippled, streaked and tessellated with close to 200C and tinged with close to 147A. Wing color, shadehouse-grown potted plants, inner surface: Close to N155C; outer surface colors and patterns visible.

Inflorescence description: Inflorescences observed on eight week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; sweet jasmine-like fragrance with camphor-like notes.

*Natural flowering season and flower longevity*.—Plants of the new *Caladium* typically flower during the spring or early summer in central Florida; flowers develop about eight weeks after growth commences; inflorescences last about three days before fading; inflorescences persistent.

*Spathe*.—Length, overall: About 9.2 cm. Length, distal open portion: About 6.1 cm. Length, proximal closed portion: About 3.1 cm. Width, distal open portion: About 4.4 cm. Width, at constriction: About 1.1 cm. Width, proximal closed portion: About 2.3 cm. Shape: Ovate to elliptic. Apex: Acuminate. Base: Tapering to the peduncle. Margin: Entire. Texture, front and rear surfaces: Smooth, glabrous. Color, front surface: Distal open portion: Close to N155C faintly tinged with close to 181 D; with development, color becoming closer to 199B. Proximal closed portion: Close to 138B and 147D; towards the base, flushed with close to 187A; color does not change with development. Color, rear surface: Distal open portion: Close to N155D tinged and faintly stippled with close to 184D. Proximal closed portion: Close to 147B to 147C tinged with close to 143B and faintly mottled with sectors of N155D and 184D.

*Spadix*.—Length: About 7.6 cm. Length, male flower zone: About 5.6 cm. Length, sterile zone: About 1 cm. Length, female flower zone: About 2 cm. Diameter, male flower zone: About 8 mm. Diameter, sterile flower zone: About 6 mm. Diameter, female flower zone: About 9 mm. Shape: Columnar, spindle-shaped. Apex: Bluntly acute. Base: Obtuse. Aspect: Upright. Color, mature, male zone: Close to 159D. Color, mature, sterile zone: Close to 159D. Color, mature, female zone: Close to 165C to 165D. Male flowers: Quantity per spadix: About 170. Shape: Obovate. Height: About 3 mm. Diameter: About 3 mm. Pollen amount: Moderate. Pollen color: Close to 4C. Female flowers: Quantity per spadix: About 156. Shape: Obovate. Height: About 3 mm. Diameter: About 1.5 mm. Stigma color: Close to 158A. Ovary color: Close to 155C.

*Scape*.—Length: About 17.8 cm. Diameter: About 6 mm. Strength: Sturdy; flexible. Aspect: Mostly erect. Texture: Smooth, glabrous; glaucous. Color: Close to 177B to 177D variably tinged with close to 147B and stippled, streaked and tessellated with close to N199B; distally, close to 147D tinged with close to 146D.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Puppy Love' as illustrated and described.

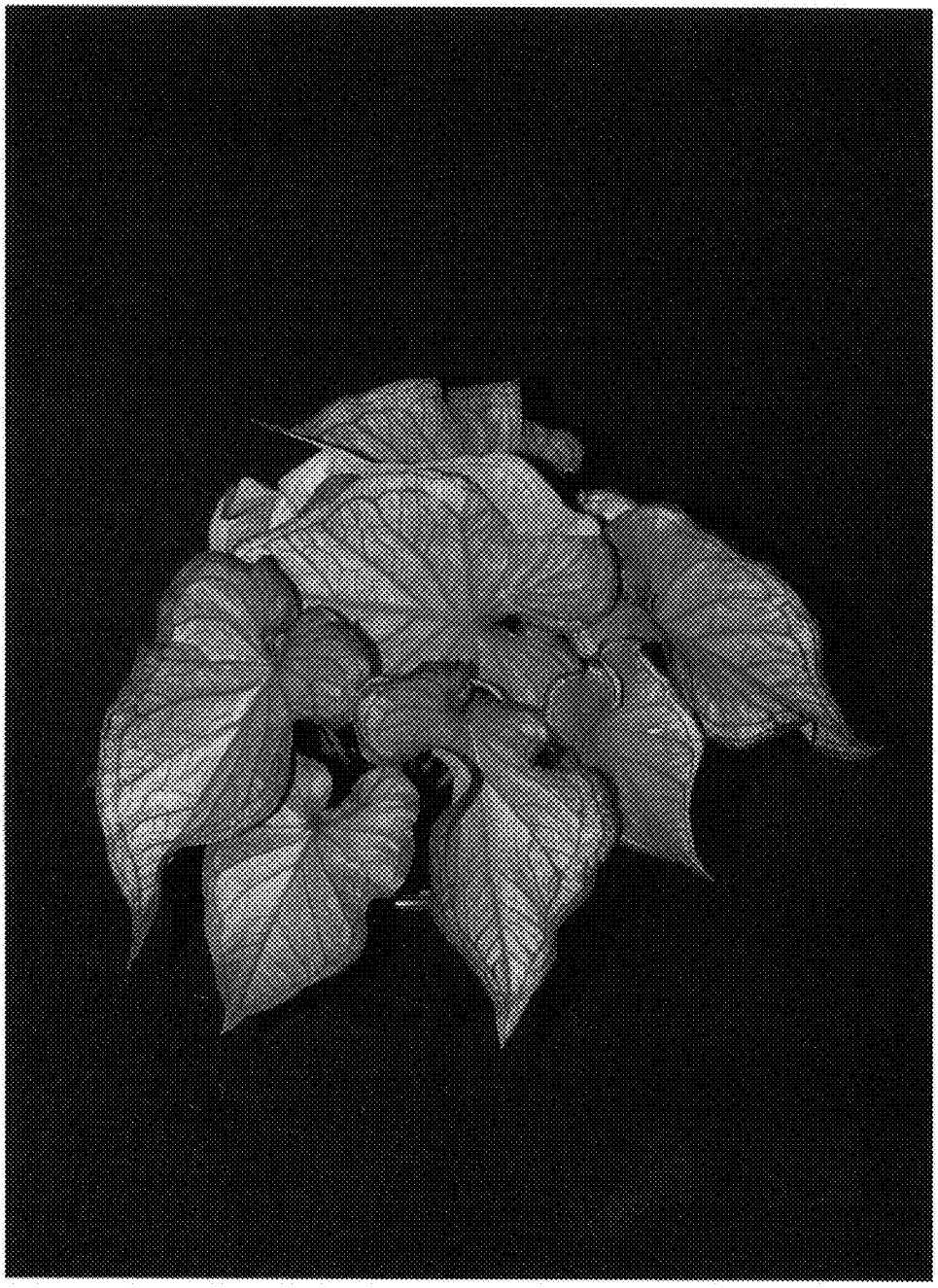

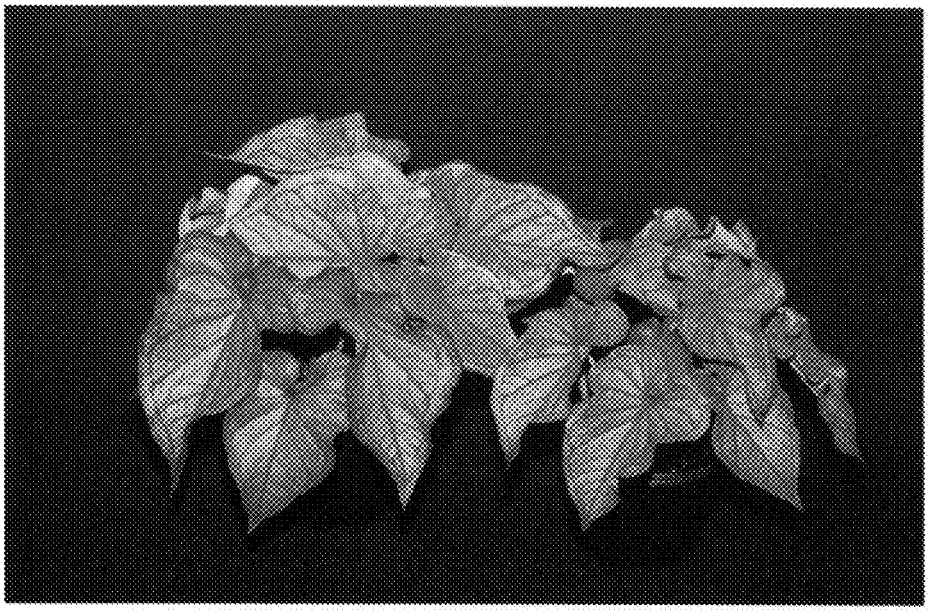
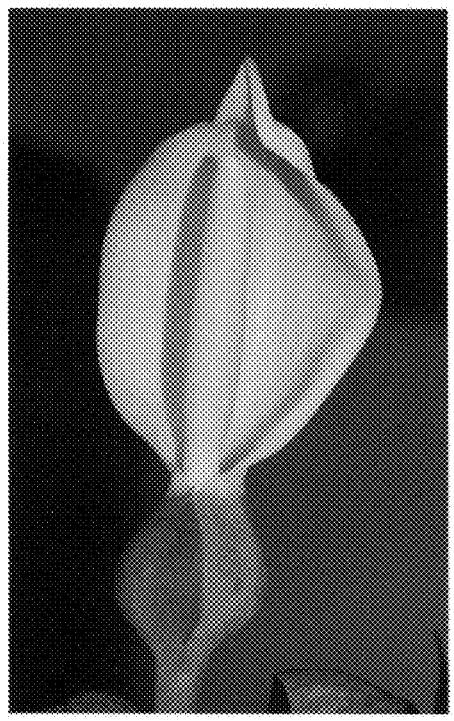

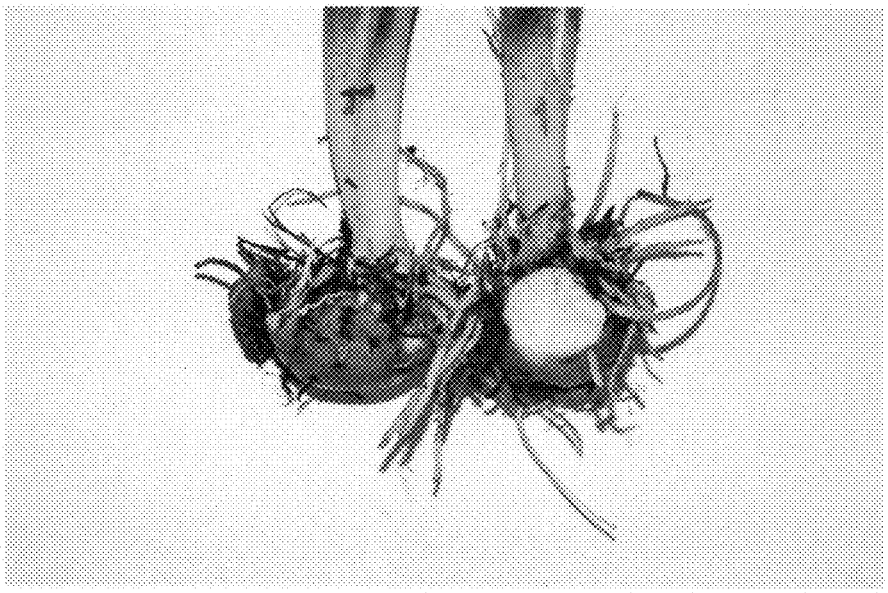
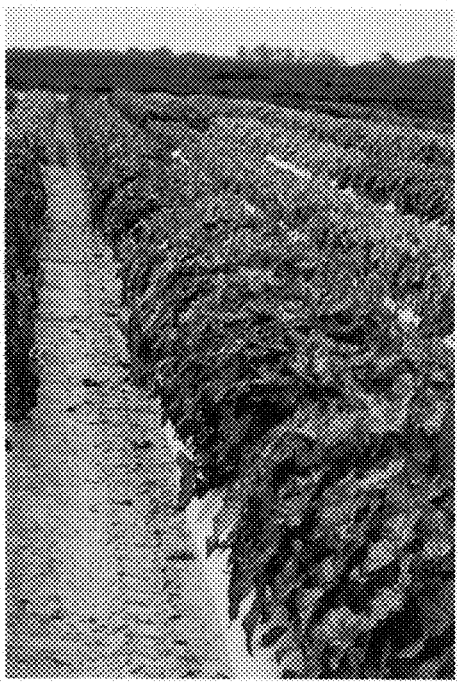

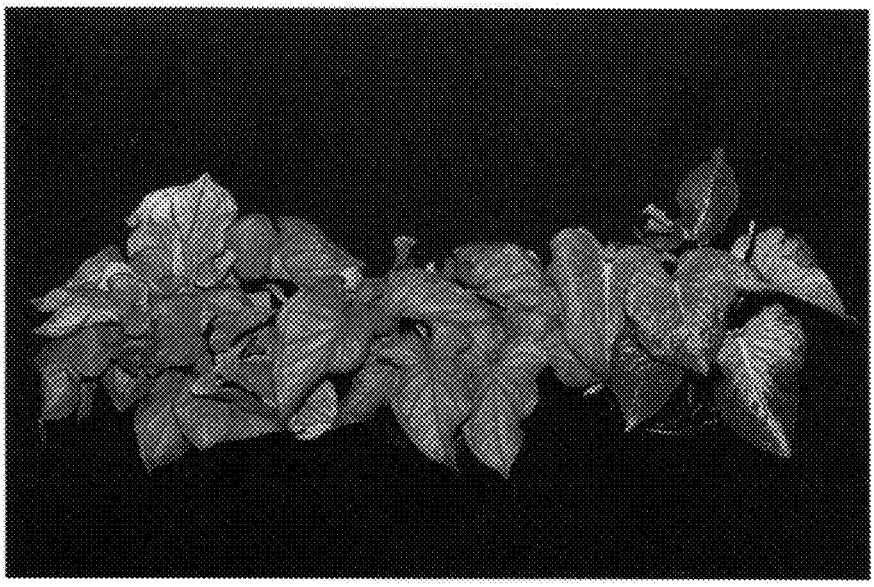
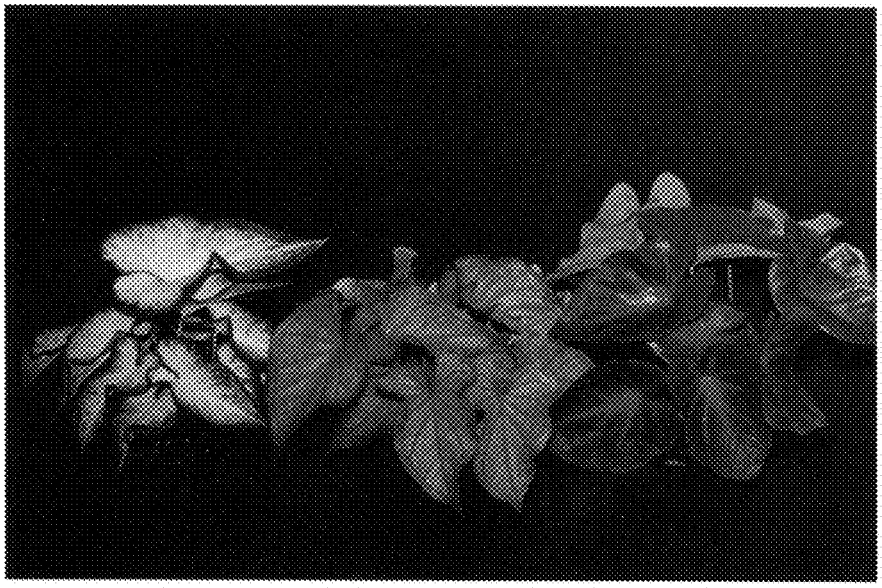

* * * * *